United States Patent [19]

Sørensen

[11] Patent Number: 5,977,069
[45] Date of Patent: *Nov. 2, 1999

[54] PHARMACEUTICAL FORMULATION

[75] Inventor: Hans Holmegaard Sørensen, Virum, Denmark

[73] Assignee: Novo Nordisk A/S, Bagsvard, Denmark

[*] Notice: This patent is subject to a terminal disclaimer.

[21] Appl. No.: 07/827,178

[22] Filed: Jan. 28, 1992

[30] Foreign Application Priority Data

Dec. 20, 1991 [DK] Denmark ................................. 2047/91

[51] Int. Cl.$^6$ .......................... A61K 38/00; A61K 38/24; A61K 9/50
[52] U.S. Cl. ............................ 514/12; 514/21; 530/324; 530/395; 530/399; 424/479; 424/499
[58] Field of Search ....................... 514/12, 21; 530/317, 530/324, 395, 399; 424/479, 499

[56] References Cited

U.S. PATENT DOCUMENTS

| | | | |
|---|---|---|---|
| 4,816,568 | 3/1989 | Hamilton, Jr. et al. | 530/399 |
| 4,917,685 | 4/1990 | Viswanathan et al. | 604/891 |

FOREIGN PATENT DOCUMENTS

| | | | |
|---|---|---|---|
| 30771/89 | 9/1989 | Australia | A61K 37/36 |
| 0 303 746 | 2/1987 | European Pat. Off. | A61K 37/36 |
| 0303746 | 2/1987 | European Pat. Off. | A61K 37/36 |
| 0 374 120 | 12/1988 | European Pat. Off. | |
| 8909614 | 10/1989 | WIPO | A61K 37/36 |
| WO 89/09614 | 10/1989 | WIPO | A61K 37/36 |

OTHER PUBLICATIONS

Johnson et al, *The Journal of Biological Chemistry*, vol. 264, No. 24, pp. 14262–14671, 1989.

Ottaway, *Biochem. J.*, vol. 136, pp. 441–444, 1973.

Yu–Chang et al., J. Parent. Sci. & Tech., vol. 42, pp. S3–S26 (1988).

Manning et al., Pharmaceutical Research, vol. 6, No. 11, pp. 903–918 (1989).

Johnson et al., The Journal of Biological Chemistry, vol. 264, No. 24, pp. 14262–14271 (1989).

Liew–Cheng Teh et al., J. of Biol. Chem., vol. 262, No. 14, pp. 6472–6477 (1987).

Becker et al., Biotech. and App. Biochem., vol. 10, pp. 326–337 (1988).

Houghten et al., Arch. of Biochem. and Biophysics, vol. 178, pp. 350–355 (1977).

Riggen et al., Analytical Biochem., vol. 167, pp. 199–209 (1987).

Gellerfors et al., Acta Paediatr Scand [Suppl] vol. 370, pp. 93–100 (1990).

Kaufman, Pharmaceutical Research, vol. 7. No. 3, pp. 289–292 (1990).

Becker et al., Biotech. and Applied Biochem., vol. 9, pp. 478–487 (1987).

*Primary Examiner*—Robert J. Hill, Jr.
*Assistant Examiner*—Abdel A. Mohamed
*Attorney, Agent, or Firm*—Steve T. Zelson, Esq.; Cheryl H. Agris, Esq.

[57] ABSTRACT

A pharmaceutical preparation comprising a growth hormone and asparagine as additive or buffering substance shows a very high stability against deamidation, oxidation and cleavage of peptide bonds. The stability of the product allows for the storing and shipment thereof in a lyophilized state or in the form of a dissolved or re-dissolved preparation at ambient temperature.

6 Claims, No Drawings

PHARMACEUTICAL FORMULATION

FIELD OF THE INVENTION

The present invention relates to a stabilized pharmaceutical formulation comprising growth hormone, to a method of making such formulation, and the use of asparagine for stabilizing a formulation of growth hormone.

BACKGROUND OF THE INVENTION

The growth hormones from man and from the common domestic animals are proteins of approximately 191 amino acids, synthesized and secreted from the anterior lope of the pituitary gland. Human growth hormone consists of 191 amino acids.

Growth hormone is a key hormone involved in the regulation of not only somatic growth, but also in the regulation of metabolism of proteins, carbohydrates and lipids. The major effect of growth hormone is to promote growth.

The organ systems affected by growth hormone include the skeleton, connective tissue, muscles, and viscera such as liver, intestine, and kidneys.

Until the development of the recombinant technology and the cloning of the growth hormone gene now giving rise to production of e.g. human growth hormone (hGH) and Met-hGH in industrial scale, human growth hormone could only be obtained by extraction from the pituitary glands of human cadavers. The very limited supplies of growth hormone restricted the use thereof to longitudinal growth promotion in childhood and puberty for treatment of dwarfism, even though it has been proposed for inter alia treatment of short stature (due to growth hormone deficiency, normal short stature and Turner syndrome), growth hormone deficiency in adults, infertility, treatment of burns, wound healing, dystrophy, bone knitting, osteoporosis, diffuse gastric bleeding, and pseudoarthrosis.

Furthermore, growth hormone has been proposed for increasing the rate of growth of domestic animals or for decreasing the proportion of fat in animals to be slaughtered for human consumption.

Pharmaceutical preparations of growth hormone tend to be unstable. Degradation products such as deamidated or sulfoxydated products and dimer or polymer forms are generated —especially in solutions of growth hormone.

The predominant degradation reactions of hGH are 1) deamidation by direct hydrolysis or via a cyclic succinimide intermediate to form various amounts of L-asp-hGH, L-iso-asp-hGH, D-asp-hGH, and D-iso-asp-hGH (Y.-C. J. Wang and M. A. Hanson, Parenteral Formulations of Proteins and Peptides: Stability and Stabilizers, J. Parenteral Science and Technology 42 (Suppl.) (1988) 53–525; M. C. Manning, K. Patel, R. T. Borchardt, Stability of Protein Pharmaceuticals, Pharmaceutical Research 6 (11) (1989) 903–918; and B. A. Johnson, J. M. Shirokawa, W. S. Hancock, M. W. Spellman, L. J. Basa and D. W. Asward, J.Biol.Chem. 264, 1462–71 (1989)), 2) oxidation of the methionine residues in positions 14 and 125 (L. C. Teh et al., J. Biol. Chem., 262, 785–794 (1987); G. W. Becker et al., Biotech. Appl. Biochem., 10, 326–337 (1988); R. A. Houghten et al., Arch. Biochem. Biophys., 178, 350–355 (1977); R. M. Riggin et al., Anal. Biochem., 167, 199–209 (1987); P. Gellerfors et al., Acta Paediatr. Scand (suppl), 370, 93–100 (1990); and M. J. Kaufman, Pharm. Res., 7 (3) 289–292 (1990)), and 3) cleavage of peptide bonds.

Deamidation especially takes place at the Asn in position 149.

hGH is rather easily oxidized in positions 14 and 125, especially in solution (4–8).

The oxidation of hGH in solution forming sulfoxides is normally due to the oxygen dissolved in the preparation. The solubility of oxygen in distilled water is about 200 $\mu$M (9). As the concentration of hGH in a preparation comprising 4IU/ml is 1.3 mg/ml corresponding to 60 nM hGH, oxygen will, at normal storing conditions, be present in an excess of about 3000 times the stoichiometric amount for oxidation of hGH. It is not feasible to try to solve the problem by degassing of buffers before tapping and packing the preparations.

At present, it is not believed that these degradation products should have toxic or altered biological activity or receptor binding properties, but there is indication to the effect that the conformation stability of the sulfoxides is reduced as compared to native hGH.

For the development of a stable, dissolved preparation comprising hGH it is of importance to know the rate of formation of sulfoxides as well as means to control the oxidation.

The kinetics of degradation depend on temperature, pH and various additives or adjuvants in the hGH formulation.

Due to the instability, growth hormone is, at present, lyophilized and stored in the lyophilized form at 4° C. until it is reconstituted for use in order to minimize the degradation.

The lyophilized pharmaceutical preparations comprising hGH are, at present, reconstituted by the patient and then stored as a solution during the use for a period of up to 14 days at 4° C., during which some degradation will take place.

Furthermore, the process of reconstitution of the lyophilized growth hormone tends to provide difficulties for the patient.

Thus, it is at present preferred to reconstitute the growth hormone as late as possible before use and to store and ship the preparation in a lyophilized state. The chain from the manufacturer to the pharmacy is apt for handling the preparations at a controlled low temperature of e.g. 4° C. which allows for a long shelf life of up to two years.

However, the extended use of pen systems for self-medication and the expanded field of use calls for a preparation which is stable for a sufficient long time with the end user under conditions where "sufficient" cooling is not always available.

Preferably, a preparation should be stable with the end user in a lyophilized state for about one month and additionally for one month in a reconstituted state in a pen device for the intended period of use of a cartridge.

Thus, there is a need for more stable preparations of growth hormone being stable in a lyophilized state at a relative high temperature for a period and additionally for a period of use at a relatively high temperature in solution. Such stabilization is of very great importance when moving the administration of the growth hormone from clinics to the homes of the individuals to be treated where optimal storage may not be available as indicated above.

Furthermore, the shift in pattern of administration of growth hormone to the use of pen devices calls for a stable dissolved preparation comprising growth hormone in order to facilitate the handling to be performed by the patient. A stable dissolved preparation comprising growth hormone may be produced ready to use in the form of cartridges fitting into the pen device used by the patient who may then avoid the reconstitution of the preparation and, hence, will not have to be in the possession of a lyophilized preparation, a suitable vehicle for reconstitution as well as the necessary skill and sterile equipment for sterile reconstitution of the preparation.

For safety reasons it will also be desirable to avoid the reconstitution of a lyophilized preparation just before the use of the preparation.

Furthermore, it would also be an advantage to avoid the lyophilization step in the production of growth hormone preparations. Lyophilization is a time consuming and costly process and is also often a "bottleneck" in the production due to the limited capacity of the freeze drier.

Thus, there is a need to reduce the rate of the degradation processes in order to allow for dissolved hGH preparations being stable during shelf life and during the period of use of up to one month.

Prior attempts to stabilize hGH has not fully succeeded in preventing the formation of dimer. The problems associated with dimer formation is e.g noted in Becker, G. W., *Biotechnology and Applied Biochemistry* 9, 478 (1987).

International Patent Publication No. WO 89/09614 and Australian Patent Application No. 30771/89 disclose a stable pharmaceutical formulation containing human growth hormone, glycine, and mannitol. Such a preparation shows improved stability during normal processing and storage in a lyophilized state as well as in the period of use after the reconstitution.

Published European Patent Application No. 303 746 discloses that animal growth hormone may stabilized with various stabilizers to give decreased formation of insolubles and preservation of the soluble activity in aqueous environments, such stabilizers including certain polyols, amino acids, polymers of amino acids having a charged side group at physiological pH, and choline salts. Polyols are selected from the group consisting of non-reducing sugars, sugar alcohols, sugar acids, pentaerythritol, lactose, water-soluble dextrans and Ficoll; amino acids are selected from the group consisting of glycine, sarcosine, lysine or salts thereof, serine, arginine or salts thereof, betaine, N,N,-dimethyl-glycine, aspartic acid or salts thereof, glutamic acid or salts thereof; a polymer of an amino acid having a charged side group at physiological pH may be selected from polylysine, polyaspartic acid, polyglutamic acid, polyarginine, polyhistidine, polyornithine and salts thereof; and choline derivatives are selected from the group consisting of choline chloride, choline dihydrogen citrate, choline bitartrate, choline bicarbonate, tricholine citrate, choline ascorbate, choline borate, choline gluconate, choline phosphate, di(choline)sulphate and dicholine mucate.

BRIEF DESCRIPTION OF THE INVENTION

It has now surprisingly been found that a preparation of human growth hormone comprising asparagine as additive or buffering substance shows a very high stability against deamidation, oxidation and cleavage of peptide bonds. The stability of the product allows for the storing and shipment thereof in a lyophilized state or in the form of a dissolved or re-dissolved preparation.

Thus, the preparation of the invention may be in the form of a lyophilized powder to be reconstituted later using conventional vehicles such as distilled water or water for injection or in the form of a solution comprising growth hormone. Such vehicles may comprise conventional preservatives such as m-cresol and benzyl alcohol.

A preferred embodiment of the invention is in the form of a pharmaceutical preparation of human growth hormone comprising asparagine and further comprising a carrier in the form of a buffered aqueous solution of growth hormone buffered with asparagine buffer. Such preparation is in a ready-to-use form and may be stored and shipped as an aqueous solution without any considerable degradation.

For stability reasons the pH of a solution is preferably adjusted to a value in the interval from 2–8.

In order to obtain the stabilizing effect asparagine is preferably added in an amount of up to 100 mM.

The pharmaceutical preparation of the invention may furthermore comprise salts and saccharides in order to facilitate the processing thereof, e.g. lyophilization.

Still another aspect of the invention relates to the use of asparagine for the preparation of a stabilized preparation of growth hormone.

In the present context "growth hormone" may be growth hormone from any origin such as avian, bovine, equine, human, ovine, porcine, salmon, trout or tuna growth hormone, preferably bovine, human or porcine growth hormone, human growth hormone being most preferred. The growth hormone used in accordance with the invention may be native growth hormone isolated from a natural source, e.g. by extracting pituitary glands in a conventional manner, or a growth hormone produced by recombinant techniques, e.g as described in E. B. Jensen and S. Carlsen in Biotech and Bioeng. 36, 1–11 (1990). The "growth hormone" may also be a truncated form of growth hormone wherein one or more amino acid residues has (have) been deleted; an analogue thereof wherein one or more amino acid residues in the native molecule has (have) been substituted by another amino acid residue, preferably a natural amino acid residue, as long as the substitution does not have any adverse effect such as antigenicity or reduced action; or a derivative thereof, e.g having an N- or C- terminal extension such as Met-hGH. The preferred growth hormone is hGH.

In the present context "high stability" is obtained when the preparation is more stable than the conventional formulation comprising phosphate buffer.

The solvent used in the method of the invention may be water, alcohols such as ethyl, n-propyl or isopropyl, butyl alcohol or mixtures thereof. The solvent may comprise a preservative such as m-cresol or benzyl alcohol.

DETAILED DESCRIPTION OF THE INVENTION

The invention is explained more in detail in the following example which illustrates the invention. They are not to be considered as limiting the scope of the present invention.

EXAMPLE

Reduction of the Deamidation

The rate of deamidation was examined at 25° C. for hGH preparations comprising 6 IU hGH at pH 6.5 in the presence of 10 mM Asn as compared to 8 mM phosphate buffer at the same pH and pH 7.3.

The hGH preparations were prepared by dissolving 20 mg hGH in 10 ml of 10 mM asparagine solution prepared by dissolving 13.2 mg, of asparagine in 10 ml deionized water containing 0.9% (v/v) of benzyl alcohol and adding 0.1N hydrochloric acid to the stated pH.

The hGH formulations stated in the following Table were stored at 25° C. and analyzed for the desamido contents after 14 and 30 days by IE-HPLC. The results appear in the following Table.

TABLE

Contents of desamido hGH as determined by IE-HPLC as a function of the formulation and the time in solution at 25° C.:

| Formulation (*) | Formation of desamido compound at 25° C. | |
|---|---|---|
| | 14 days (') | 30 days |
| 8 mM di-Na-Phosphate pH 6.5 | 7.8 | 10.8 |
| 8 mM di-Na-Phosphate pH 7.3 | 15.2 | 20.3 |
| 8 mM di-Na-Phosphate pH 6.5, 0.3% m-cresol | 9.4 | 13.2 |
| 10 mM Asp, pH 6.5 | 21.7 | nd |
| 10 mM Asn, pH 6.5 | 6.5 | 8.3 |
| 10 mM Glu, pH 6.5 | 14.8 | nd |

*: Comprises 0.9% benzyl alcohol except formulation # 3.
The contents of desamido-hGH in starting material was: 2.1%.

From the above Table it appears that the de-amidation of hGH is reduced by approximately 25% by the addition of asparagine as compared with phosphate buffer at ph 6.5.

Addition of Asp or Glu increases the rate of deamidation as compare to phosphate at pH 6.5.

The above results show that the rate of de-amidation is reduced by lowering the pH and by adding asparagine in a low concentration of up to 100 mM, preferably about 5 mM.

The rate of de-amidation may be reduced by more than 50% by lowering the pH and substituting the phosphate buffer with asparagine.

The use of m-cresol or benzyl alcohol as preservative seems to have no influence on the rate of de-amidation.

Split-formation (hydrolysis of peptide bonds) is reduced by asparagine at pH 6.5 in comparison with phosphate.

I claim:

1. A pharmaceutical preparation of growth hormone comprising a stabilizing amount of asparacine wherein the pH of said preparation is adjusted from 2–8.

2. The pharmaceutical preparation according to claim 1, further comprising a carrier in the form of a buffered aqueous solution of growth hormone containing asparagine.

3. A pharmaceutical preparation as claimed in claim 1 wherein the concentration of asparagine is greater than 0 mM and no more than 100 mM.

4. A pharmaceutical preparation as claimed in claim 1 which further comprises salts and saccharides.

5. A pharmaceutical preparation as claimed in claim 1 wherein the growth hormone is human growth hormone.

6. A method for stabilizing a formulation of human growth hormone comprising combining human growth hormone with asparagine, wherein the concentration of asparagine is greater than 0 mM and no more than 100 mM.

* * * * *

UNITED STATES PATENT AND TRADEMARK OFFICE
CERTIFICATE OF CORRECTION

PATENT NO. : 5,977,069
DATED : November 2, 1999
INVENTOR(S) : Hans Holmegaaard Sorensen It is certified that error appears in the above-identified patent and that said Letters Patent is hereby corrected as shown below:

Col. 6, line 10, cl. 1    delete "asparacine" and insert --asparagine--

Signed and Sealed this

Eighth Day of May, 2001

Attest:

NICHOLAS P. GODICI

Attesting Officer    Acting Director of the United States Patent and Trademark Office